United States Patent [19]

Franklin et al.

[11] 4,300,689
[45] Nov. 17, 1981

[54] DUAL WAVELENGTH SPECTROPHOTOMETER FOR AMPOULE LEAK DETECTION AND CONTENT INSPECTION

[75] Inventors: Michael L. Franklin, Parsippany; Charles W. Jeunelot, Wayne, both of N.J.

[73] Assignee: Hoffmann-La Roche Inc., Nutley, N.J.

[21] Appl. No.: 180,249

[22] Filed: Aug. 22, 1980

Related U.S. Application Data

[63] Continuation of Ser. No. 91,602, Nov. 5, 1979, abandoned, which is a continuation of Ser. No. 869,554, Jan. 16, 1978, abandoned.

[51] Int. Cl.³ .................................................. B07C 5/342
[52] U.S. Cl. .................................... 209/524; 209/3.3; 209/588; 73/41.4; 73/45.5; 250/223 B; 356/407; 356/418
[58] Field of Search ............... 209/3.1, 3.3, 524, 551, 209/588; 356/407, 418, 419; 250/223 B, 227, 565; 73/40.7, 41.4, 45.4, 45.5, 49.3

[56] References Cited

U.S. PATENT DOCUMENTS

| | | | |
|---|---|---|---|
| 2,479,743 | 8/1949 | Hall et al. | 73/45.5 |
| 2,905,318 | 9/1959 | Schell | 209/524 |
| 3,043,179 | 7/1962 | Dunn | 250/227 |
| 3,676,007 | 7/1972 | Kiess | 356/419 X |
| 3,843,258 | 10/1974 | Shupe | 356/407 |

Primary Examiner—Joseph J. Rolla
Attorney, Agent, or Firm—Jon S. Saxe; Bernard S. Leon; Frank P. Hoffmann

[57] ABSTRACT

A dual wavelength spectrophotometer for ampoule content inspection, in particular for ampoule leak detection wherein leaks are initially "flagged" via the dye bath immersion technique. Light transmitted through the ampoule is received by a bifurcated fiber optic cable providing via a random mix arrangement substantially identical ampoule optical signature signals. Each is directed through preselected interference filters, chosen on the one hand on the basis of the dye being used and the glass ampoule and its contents on the other hand. Associated with the filters are respective photodetectors, the output signals of which are connected to a difference amplifier stage. The output (if any) of the latter is compared to a preestablished (dye) threshold signal, which represents the minimum level (of dye) from which to effect a reject status. The ampoule contents or a particular component thereof may also be investigated in this manner. The photodetector outputs are also summed and the resultant compared to a second preestablished threshold in order to provide a failsafe system capability against optical failure and the like. The difference signal/comparison circuit leg may be constructed to provide logrithmic function capability and thus produce an output which a proportional to concentration. Therefrom the concentration of the ampoule contents (or the dye) can be determined, for example to lie within a preestablished "window".

5 Claims, 11 Drawing Figures

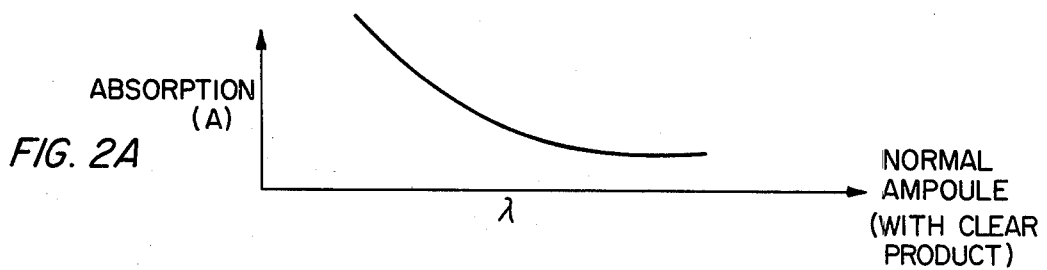
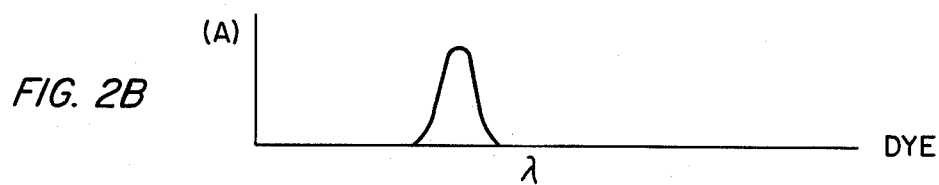
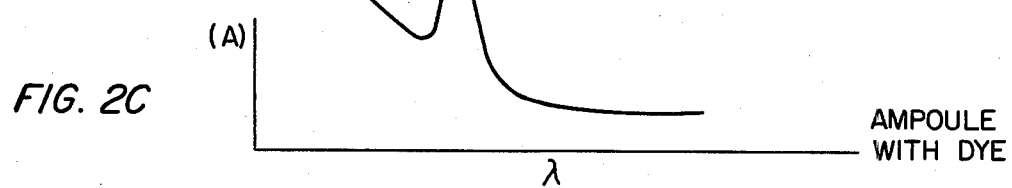
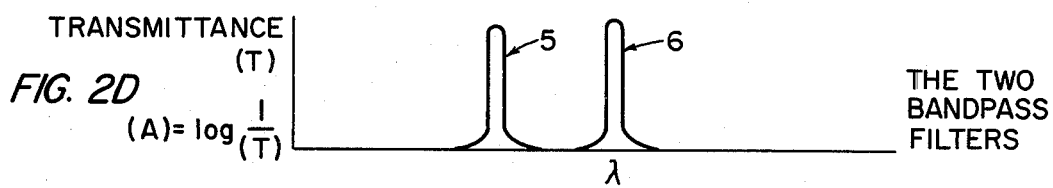
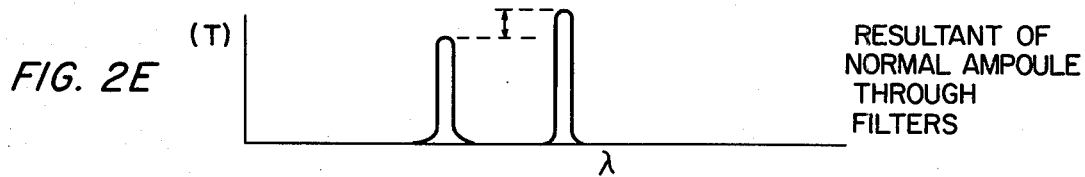
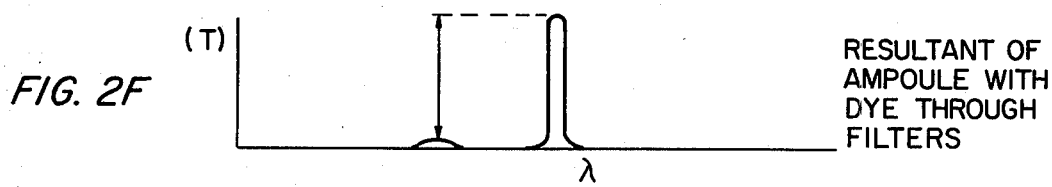

DUAL WAVELENGTH SPECTROPHOTOMETER FOR AMPOULE LEAK DETECTION AND CONTENT INSPECTION

This is a continuation, of application Ser. No. 91,602, filed Nov. 5, 1979 now abandoned, which in turn is a continuation of Ser. No. 869,554, filed Jan. 16, 1978, now abandoned.

BACKGROUND OF THE INVENTION

This invention relates to the detection of leaks in containers (e.g. ampoules) and more particularly to the optical detection of leaks in ampoules based on the dye bath technique.

The detection of leaks in sealed containers has been a problem for many years. Depending upon the container and its contents leaks could be a hazard to life and property; for example, a leaking canned good could lead to food poisoning. Methods used in detecting leaks are perhaps as varied as the types and kinds of containers available and the materials to be found therein.

The particular container of major interest regarding this invention is the ampoule generally used to contain a pharmaceutical substance. The ampoule is a substantially cylindrical, generally glass container, usually transparent or translucent, having a flat base and a rounded-off top portion of reduced cylindrical dimension sitting atop an even narrower neck portion. Glass ampoules are extensively used in the pharmaceutical and chemical industries for the storage and shipment of solutions of drugs and chemicals, both liquid, gases and solids.

The ampoule is normally filled with the desired substance via the top portion, and therefollowing a glass seal is effected at the tip. The primary location of leaks is, as might be expected, associated to this final seal at the tip of the ampoule.

Even today, such seals are inspected visually by human inspectors inverting, shaking and holding the ampoule up to a strong diffuse backlight. It is, of course, of fundamental importance, considering the nature of the substances under particular consideration here, that the ampoule seal be absolutely complete, or the contents of the ampoule may become contaminated.

It has been discovered that, although the seal appears to be perfect, the filled ampoule may start to leak a minute quantity after only a short time and/or over a more extended period.

Heretofore, detection of such leaks was effected by exposing the ampoule to some substance that was known to react with the ampoule contents and which would leave a visible reaction product. Hopefully, even minute leakages would leave a visible indication and the affected ampoule would be correspondingly removed from the lot.

However, not only must the chosen substance to which the ampoule is to be exposed be able to react with the ampoule contents, the amount of visible reaction product is necessarily limited to being proportional to the amount of contents brought into contact with the reacting substance (i.e. that have leaked out or viceversa). For very small leaks, sometimes called microleakers, the reaction product is obviously correspondingly very small. such circumstances make the detection of very small leaks difficult especially with the ampoules being visually inspected by humans for the presence of the reactant. Nevertheless, this step constituted an improvement over unaided human inspection.

Another known method of detecting leaks in ampoules may be generally identified as the bubble detection technique. This technique involves compressed air being applied via a (Plexiglass) nozzle arrangement to the top portion of the ampoule. The positive pressure is constantly applied and of known value. The ampoule is oriented upside down in the nozzle with the liquid in the ampoule thus completely filling the top portion. Each ampoule remains under test over a set period of time, generally one minute, and is assumed good if no bubbles are detected in that time. Inspection is normally performed by human beings, although seemingly could instead be performed by some sort of suitably arranged bubble detector.

The bubble detection method, in addition to being limited by the inherent problems associated to human visual detection or by the need for expensive bubble detection arrangements, is also rather restricted in effectness to the exact portion of the ampoule being placed under pressure, and most of the exterior surface of the ampoule thus goes uninspected. Also, such a technique does not lend itself to the high volume industrial environment.

A further existing method involves detection of leaks by establishing a loss of weight. In this method a vacuum is applied to the ampoule and a subsequent weighing performed. Although such a method may be satisfactory under laboratory conditions, the inherent complexity and slowness alone involved in weighing each ampoule separately (and twice), as would be necessary particularly in regard to ampoules containing pharmaceutical substances, and particularly in an on-line industrial environment, would generally rule this technique out as an acceptable alternative.

The search for a better technique for detecting the existence of leaks in ampoules has in recent years centered upon the now U.S. FDA-accepted technique of exposing the ampoules to a dye solution. With an incomplete seal the contents of an ampoule could leak out, and if such an ampoule were placed in a dye solution, a certain amount of the dye should be able to "leak in". Since ampoules generally are filled and sealed at atmospheric pressure the dye diffusion rate into the ampoule could be increased by placing the ampoule and dye bath in a suitable temporarily pressurized (positive pressure) environment. The results for a leaky ampoule will normally be a dye tint within its contents.

More particularly, seal integrity of the ampoules is usually checked at the present time by the complete immersion of each ampoule in a concentrated blue dye solution (e.g. $25 \times 10^{-6}$ g/ml of Food Drug and Cosmetic (FD&C) blue #1 triphenylmethane dye), with a vacuum pressure of twenty-eight inches of mercury being established for thirty minutes. Upon release of the vacuum the concentrated dye is drawn into the ampoules through any small leaks in the glass. Subsequent handling of the ampoules mixes the dye and its color is detected visually by the inspectors who then reject those leaky ampoules.

It will be apparent that the dye "flagging" technique also suffers from at least the two factors of: (1) the viewability of the "flag" being proportional to its concentration within the ampoule contents; and (2) the detection of the "flag" remaining in the work task of human inspectors. For example, it has been determined experimentally that for a given commercially available product, 1.08 micrograms of dye per ml of solution was the minimum concentration detectable (zero defects level of detection) by the inspectors using diffuse light panels to backlight the ampoules. This figure is a function of ampoule and compound tubidity and color.

The above-quoted figure, although somewhat impressively small, by no means lays to rest the question of whether smaller leaks with correspondingly smaller dye concentrations can exist, and whether such leaks can be tolerated. It has been found that smaller leaks do exist; and depending upon the substance of interest, especially a pharmaceutical product, it is entirely unlikely that any detectable leakage could be tolerated. For example, ampoules passing such tests as have been described hereinabove have later been demonstrated to have holes, as indicated by the presence of dried material on the outside near the seal. Microscopic examination thereof has shown that the holes can have external diameters of approximately 40 $\mu m$, narrowing to about 3 $\mu m$ typically.

One of the more recent and rigorous leak tests that has been developed to prove the structural integrity and sterility of ampoules involves placing for example a helium atmosphere in the ampoule prior to sealing. Following sealing and sterilization, the ampoule is tested with a mass spectrometric leak detector for the passage of helium. Using a mass spectrometer with a sensitivity limit of say $1 \times 10^{-10}$ standard cm$^3$ of He/s, it is calculated that a hole 0.9 $\mu m$ in diameter and with a length of 1 mm would be detectable with a leak rate of $3.5 \times 10^{-8}$ standard cm$^3$/s. (Bacteria cannot pass through holes this small.) This technique could also be applied with nitrogen or air atmospheres.

Although perhaps even more rigorous tests can or have been developed, such techniques are, for industrial purposes, generally far too complex, slow and cumbersome, especially for handling of large volumes of throughput, and involve expensive equipments requiring highly trained personnel.

Several other prominent factors facing a manufacturer of the kinds of products with which this discussion relates contribute to the need for an improved system for inspecting filled ampoules. These include the desire to increase the speed of the inspection process, particularly in a high volume industrial environment, and to remove the troublesome inter- and intra-inspector differences, as well as enable the detection of the presence of lower dye or other "flag" concentrations (e.g. microleakers).

SUMMARY OF THE INVENTION

It is thus a principal object of this invention to provide, particularly for relatively high-speed, high volume industrial environments, a fully automated, on-line inspection system for the detection of leaks in ampoules, even microleaker situations bordering on the threshold of detectability by highly elaborate equipment, which system is comprised of an inexpensive and uncomplicated optical arrangement.

It is another object of this invention to provide an ampoule inspection system of the above-mentioned type that makes use of a government-accepted ampoule leak detection process in a more reliable and sensitive way and which enables virtual elimination of human inspection and the inherent risks of error associated therewith such as arises from inspector fatigue or differences in sensitivity.

It is a further object of this invention to provide such an optical inspection system in a transmissive mode arrangement grounded on the dye-detection technique, with fail-safe capability to detect properly even those cases where the ampoules are practically opaque due to dye concentrations resulting from gross leaker situations as well as when the level of liquid in the ampoule is significantly less than the proper amount (e.g. below the level point at which the inspection optics are aimed).

It is yet another object of this invention to provide an ampoule leak detection system which generates output signals for ampoule rejection which leads to the physical removal of the unacceptable ampoules from the production line.

According to the broader aspects of the invention there is provided a dual wavelength spectrophotometer for use in connection with container content inspection and in particular container leak detection, comprising in combination:

(a) a source of radiant energy;

(b) first means arranged to receive radiant energy from said source which has passed through the container and its contents for generating simultaneously a plurality of substantially identical optical signals constituting optical signatures of the container and its contents;

(c) a plurality of predeterminably selected unique radiant energy filter means arranged to each receive a said optical signal from said first means;

(d) a plurality of photodetector means arranged with said filter means for providing a plurality of respective output electrical signals representative of the radiant energy received from said filter means; and (e) second means for determining the difference between at least a selected first pair of said respective output electrical signals and comparing said difference with a pre-established first threshold value.

In a preferred arrangement there is provided a bifurcated fiber optic, dual wavelength interference filter photometer arrangement to detect the presence of even ultra-low levels of, for example, FD&C No. 1 blue dye. A light source (e.g. tungsten) is used to provide spectral radiation matched to the dye absorption and the photodetectors' response curves. After passing through the ampoule to be inspected (it is to be noted that a non-opaque, liquid-filled ampoule will act like a double-convex lens to light incident on the side thereof), the transmitted light is equally divided into two beams by a random mix, bifurcated fiber-optic bundle. The split beams pass through interference filters, which isolate the area of blue dye absorption and reference absorption due to the glass ampoule (and its contents) respectively. The light beams are detected by a pair of photodetectors (e.g. photodiodes) and amplified. A further amplifier is employed to measure the difference between these two signals. A threshold comparator determines when there is an imbalanced signal which indicates the presence of dye, turbid/opaque ampoules, or empty ampoules.

Provision is also made to render the system fail-safe by detecting the sum of the two signals. This detects substantially completely opaque samples and also system failure (e.g. light-source failure).

The fact that the shape of the ampoule causes it to act like a double convex lens arrangement aids in on-the-fly inspection, i.e. the ampoule's shape yields a pronounced optical signature. However, it is not essential to the invention that the inspected object be cylindrical in cross-section; practically any cross-sectional shape would be operative.

It should be noted that by providing a vertical geometry to the entrance aperture of the fiber optic cable (i.e. manufactured or masked), there is effected an optimization of the light gathering process from the already existing focusing effect of the ampoule itself, as described herein. This, of course, would permit a substantial reduction in the degree of randomness to be otherwise provided by the bifurcated fiber optic cable.

Moreover, it is to be noted that while any suitable light source filters and photodetectors may be used, it is preferable to match the intensity and the wavelength spectrum of the light source to the spectral response of the light detectors. The filters, however, should largely control the detectors employed, and are in turn controlled by the transmission spectrum of the ampoule and its contents.

It should be noted further that a beam splitter may be provided in place of the bifurcated fiber optic bundle. Also, the invention is not limited to the visible electromagnetic radiation spectrum. Depending, for example, on the color of the ampoule and its contents, the reference wavelength could very well be selected in the infra-red or ultraviolet range. For those situations involving an infra-red range a beam splitter would tend to be advantageous, whereas a quartz fiber optic bundle would be preferable for the ultraviolet range, and the fiber optic bundle for the visible range would typically be of glass.

It is to be particularly noted that any difference between the two optical paths will remain relatively constant for changes in ampoule contents and source. The difference factor will change with the introduction of dye since only one path is affected.

The advantages of using the comparison or dual wavelength technique include reduced degradation from background light changes and common mode interference, as well as reduced stability requirements on the detectors. Moreover, in relation to the present technique involving manual inspection, errors in judgment due to inspector fatigue and differences in sensitivity between inspectors have thus been eliminated.

Also, the dual wavelength photometer inspection system according to the invention is considerably faster than present systems (for example ten ampoules per second for a serial throughput). Of perhaps greatest importance however, is the fact that a system according to the invention has already been shown to be sensitive to between one-eighth and one-sixteenth the dye concentration level detectable by human inspectors, yet involves only an inexpensive and uncomplicated arrangement in doing so.

These latter points are further appreciated when it is considered that the present speed of the human inspector (i.e. the human inspector throughput) is on the average of one ampoule every three seconds for the final inspection task.

More particularly, the dual wavelength photometer system according to the invention has already been demonstrated to have achieved a zero defects concentration level of $6.3 \times 10^{-8}$ g/ml. From this initial dye solution concentration and the following equation:

$$\frac{6.3 \times 10^{-8} \text{ g/ml } 2.2 \text{ml}}{2.5 \times 10^{-5} \text{ g/ml}} = X \text{ ml, or } X = 5.5 \times 10^{-6} \text{ liters,}$$

it is shown that as low as six nanoliters of dye leaking into a two-ml (e.g. flint) ampoule can be reliably detected. Assuming twenty-five drops per ml, then only 1/10 of a drop is the leakage required at present stages of development for reliable detection with the dual wavelength photometer system according to the invention.

Inasmuch as the actual color of the glass ampoule containers and the contents contained therein vary from situation to situation, the reference wavelength and the target wavelength necessarily may be different for each situation. Notwithstanding, in the system according to the invention the modification required to handle each situation amounts to no more than selection of the appropriate interference filters (and, as appropriate, detectors) to best fit that particular situation. For example, the filters could be mounted on a rotary wheel or other suitable arrangement having N number of filter pairs which can be selected at will for any particular sample inspection or analysis. Such a filter selection arrangement may be employed to provide multiple reference/target pairs for sample (i.e. ampoule contents) analysis, for example to check for the presence of each of the intended constituents of that sample as well as whether dye is present or not. Provision may be made to have the filter selection programmable for fast (e.g. stepped) sequencing through all preselected filter pairs. Such an arrangement would also be particularly applicable for the processing of a new sample to determine which wavelength(s) would be best used as the reference wavelength(s) for that particular lot run. It is recognized that detection should be synchronized to filter selection.

A further advantage regarding the dual wavelength technique according to the invention is the fact that the same is not affected virtually in any way by small irregular movement of the ampoules past the optics, such as is sometimes experienced in the ampoules jostling along the production line. This is so primarily because of simultaneous consideration at both the target and reference wavelengths of the light passing through the ampoule.

It should also be observed that the present invention is not restricted to dual wavelength technique, but rather encompasses the possibilities of N-wavelength (e.g. quadrawavelength) simultaneous analysis. It will be appreciated that as N increases, with judicious selection of the various wavelengths, a more precise signature of the ampoule and its contents is obtainable, for even more accurate processing.

Within the scope of this invention also is the employment of, for example, a quadrafurcated fiber optic cable arrangement leading to two channels of essentially the same processing electronics, as hereinabove described, one arranged (tuned) for blue dye detection and the other to ensure that even in the case of the good ampoule, the contents thereof possess the correct color.

BRIEF DESCRIPTION OF THE DRAWINGS

The above-mentioned and other objects and features will become more apparent and the invention itself better understood by reference to the following detailed description taken in conjunction with the accompanying drawings, in which:

FIGS. 2A-2F are graphic representations of the operation of various aspects of the system of FIG. 1;

DESCRIPTION OF THE PREFERRED EMBODIMENT(S)

Figure 1:
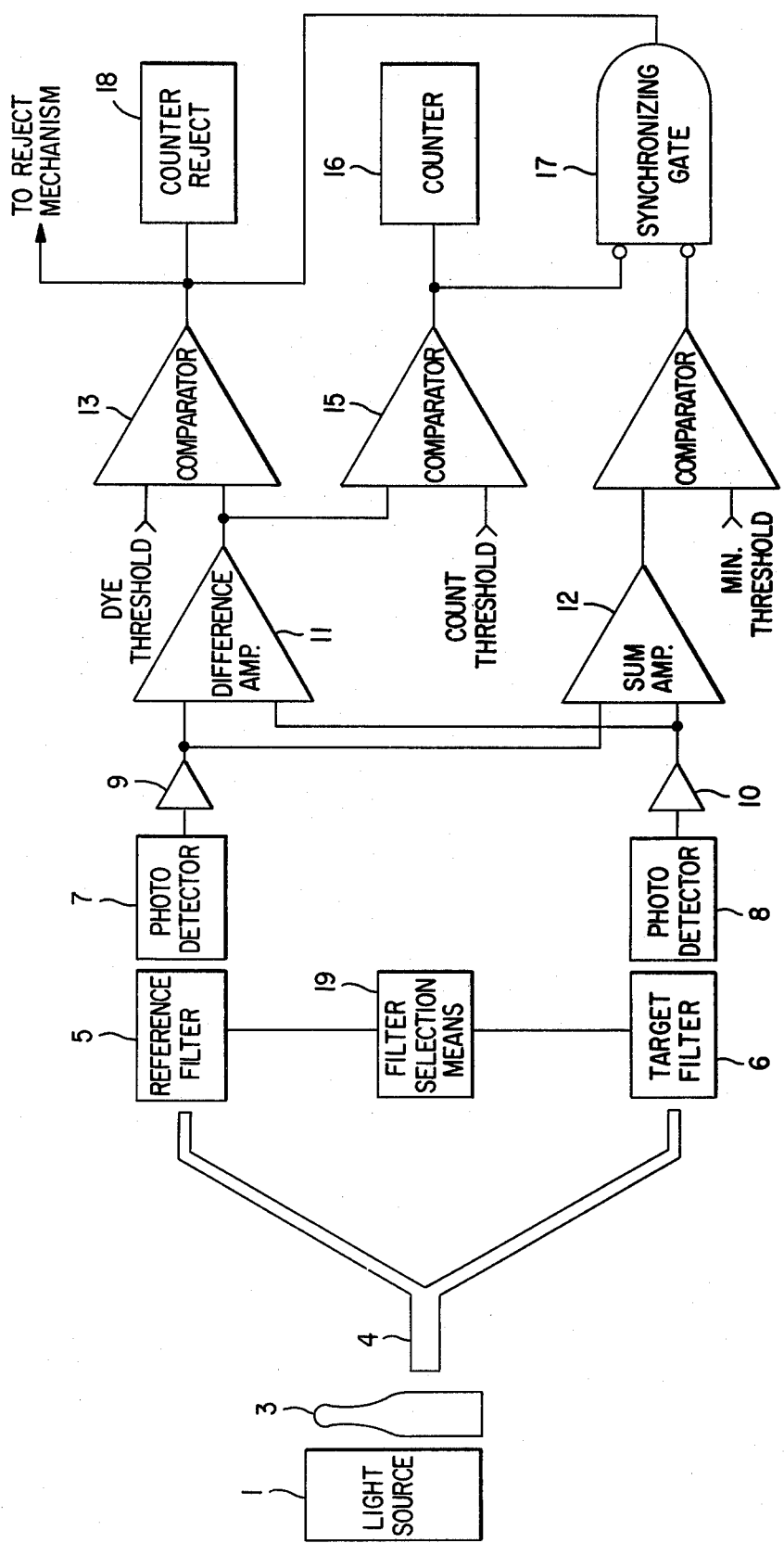
FIG. 1 is a schematic diagram of a dual wavelength ampoule leak detection system in accordance with the invention.

Reference is made to FIG. 1 which illustrates schematically a preferred arrangement of dual wavelength spectrophotomer according to the invention for the detection of the presence of dye in sealed ampoules. The ampoules 3 pass in single file via a suitable transport mechanism (not particularly shown) through an optical arrangement comprising on the one hand a light source 1 and there opposite the receiving aperture of a bifurcated fiber-optic cable. Taking into consideration the aforementioned property of the glass ampoules, the receiving aperture of the bifurcated cable is able to easily pick up this rather sharply defined light pattern for each ampoule, even at relatively high speeds of throughput.

The preferred type of fiber-optic cable 4 splits at some point along its length into a pair of individual cables in which the fibers are randomly located to yield a uniform mix, i.e. the minute segments are randomly distributed in the resulting transmission cables. Bifurcation in this manner yields a pair of virtually identical (light) radiant energy signals, thus facilitating the comparison(s) to be made in accordance with the invention.

Each one of the pair of radiant energy signals is guided by the associated bifurcated portion of the fiber optic cable to be incident upon a respective narrow passband filter 5, 6. One of these filters is chosen to have the center wavelength thereof correspond to a wavelength falling well within a strong passband of the ampoule and its contents and which does not overlap or fall within the passband of the dye at all (e.g. filter 5). The other is chosen with the center wavelength thereof falling within the or a strong passband of the combination of the dye, the ampoule and the latter's contents (e.g. filter 6). It is preferable that the filters not have overlapping passbands.

Light incident upon and passing through the respective interference filters 5 and 6 is directly received by respective photodetectors 7, 8. Photodetectors 7 and 8 preferably may take the form of photodiodes. Photodetectors 7 and 8 convert the optical signals received thereby to respective electrical signals which in turn are individually fed to corresponding current/voltage converters 9, 10. The respective outputs of converters 9 and 10 are on the one hand fed to a difference amplifier 11 and on the other hand to a summing amplifier 12. In stage 11 the difference between the two output signals of converters 9 and 10 is determined, and would be "zeroed-out" (insignificant) in the case of a good ampoule.

In order to provide a margin of noise immunity (it has, for example, been found in practice that there can be a sensitivity even to fingerprints on the ampoule glass) and a switching scheme, the output of difference amplifier stage 11 is connected to a comparator stage 13. Thereby, a threshold may be established as to which the signal output from the difference amplifier stage 11 must exceed in order to indicate dye presence in the ampoule. The other input of comparator 13 is thus identified in FIG. 1 as the dye threshold input, which may be set in accordance with empirical determination or a standardized sample.

It should be noted that the amount of change from the "zeroed" difference would be a relative indication of the presence of dye in the ampoule. It will nevertheless be appreciated that no signal is output from comparator state 13 unless the presence of dye (and therefore a leaky ampoule) has been detected. The output (if any) of the dye detection comparator stage 13 is coupled to the ampoule rejection mechanism (not particularly shown) and may also be coupled to a reject counter stage 18.

In regard to the aforementioned setting of the dye threshold input of comparator stage 13, several standardized samples can be prepared with specific and different fractional levels of blue dye concentration (including one having no blue dye present in its contents). These standards may, however, be marked (e.g. the tips color-coded) so as to be each easily identifiable apart from the regular throughput and from each other. The standardized samples may, in terms of relative concentration of blue dye, effectively run for example from the equivalent of the human zero defects level down to ⅛ and 1/16 thereof. Presently, it has been observed that rejection of some good ampoules has occurred where the dye threshold input has been set to allow the 1/16 level concentration standard to pass through the system unrejected. This has been observed to result from the aforementioned problems of fingerprints, foreign films etc. on the ampoules. It has thus been found appropriate at present to set the dye threshold input of comparator 13 to enable the 1/16 concentration standard sample to easily pass through the system unmolested whereas the ⅛ concentration standard sample should be rejected. In this way also, once the threshold is properly set the ⅛ to 1/16 standard samples can be periodically (e.g. every 10,000 ampoules) inserted into the production line to ensure that the system is operating properly.

As a means of ensuring that the system knows in each instance when it is observing an ampoule passing through the optical front-end of the system according to the invention, the output from difference amplifier stage 11 is coupled to a second comparator stage 15, having its other input identified in FIG. 1 as a count threshold (conventionally derived). The count comparator 15 output is in turn fed to a counter arrangement 16 thus providing for the system the total count of throughput during an inspection run.

A second circuit leg, comprising summing amplifier stage 12, has been included in the arrangement according to FIG. 1 in order to provide for fail-safe operation, and especially to enable the system to successfully handle open or grossly dye-concentrated (practically opaque) ampoules, system failure (such as the light source 1 failing altogether), and also to detect situations where ampoules are substantially underfilled.

Each of the above-indicated system capabilities is provided by the amplifier stage 12 summing the two output signals of converter stages 9 and 10, thereby generating an output which is connected to yet a third comparator stage 14. The other input of comparator 14 is identified in FIG. 1 as a minimum threshold input. Comparator stage 14 determines whether the signal from summing amplifier stage 12 falls below a pre-established minimum threshold. Thus, if any one of the following occurs, such as an opaque ampoule, a foreign object being inspected, light source failure or blockage, blockage of the light path such as would occur if the input end (or one of the output ends) of the fiber-optic bundle becomes grossly misaligned, photodetector failure, etc., the result will be a failure to achieve the pre-established threshold. Comparator stage 14 would thus in any of these events generate a rejection signal.

It should be noted, keeping in mind the natural focusing effect of an ampoule, which in turn gives rise to a pronounced and relatively sharp optical signature, that there is a substantial difference (degradation) in the signature if the ampoule is empty or grossly underfilled (i.e. the level of liquid content falls below the level at which the optical arrangement is aimed). Thus, the minimum threshold input of comparator stage 14 may be set in accordance with empirical determinations to take into consideration the level of signature normally received by a properly filled ampoule vis-a-vis the substantially reduced signature which occurs in the case of the underfilled or empty ampoule.

The rejection signal output of comparator 14 (if any) is coupled to a synchronizing AND gate 17, the other input of which is the output of count comparator stage 15. AND gate 17 will thus only provide an output rejection signal as and when the system has determined the presence of an ampoule for inspection. The output of AND gate 17 may, like the output of dye level comparator stage 13, be forwarded to the rejection mechanism, and may also be connected to counter stage 18.

In operation, reference is made to FIGS. 2A-2F illustrating in particular the spectral responses of or caused by the ampoule, the dye, the filters, and certain combinations thereof. FIG. 2A is representative of the spectrophotometer output for a normal filled ampoule, where the horizontal axis represents wavelength ($\lambda$) and the vertical axis absorption/concentration. On the other hand, FIG. 2B illustrates a representation of the spectral response provided by the chosen dye (i.e. the blue dye identified hereinbefore). An ampoule with a significant amount of such dye is likely to provide the general spectral response illustrated in FIG. 2C.

FIG. 2D shows representations of the spectral characteristics of the bandpass filters 5 and 6, and FIG. 2E demonstrates the resultant light transmitted through the filters in the case of a normal ampoule being inspected. On the other hand FIG. 2F demonstrates the spectral response of the interference filter (5 and 6) components of the system deriving from inspection of an ampoule containing a significant amount of blue dye. In FIG. 2F one can perceive the substantial difference in magnitudes at these two wavelengths for an ampoule having dye present within its contents.

Figure 3:
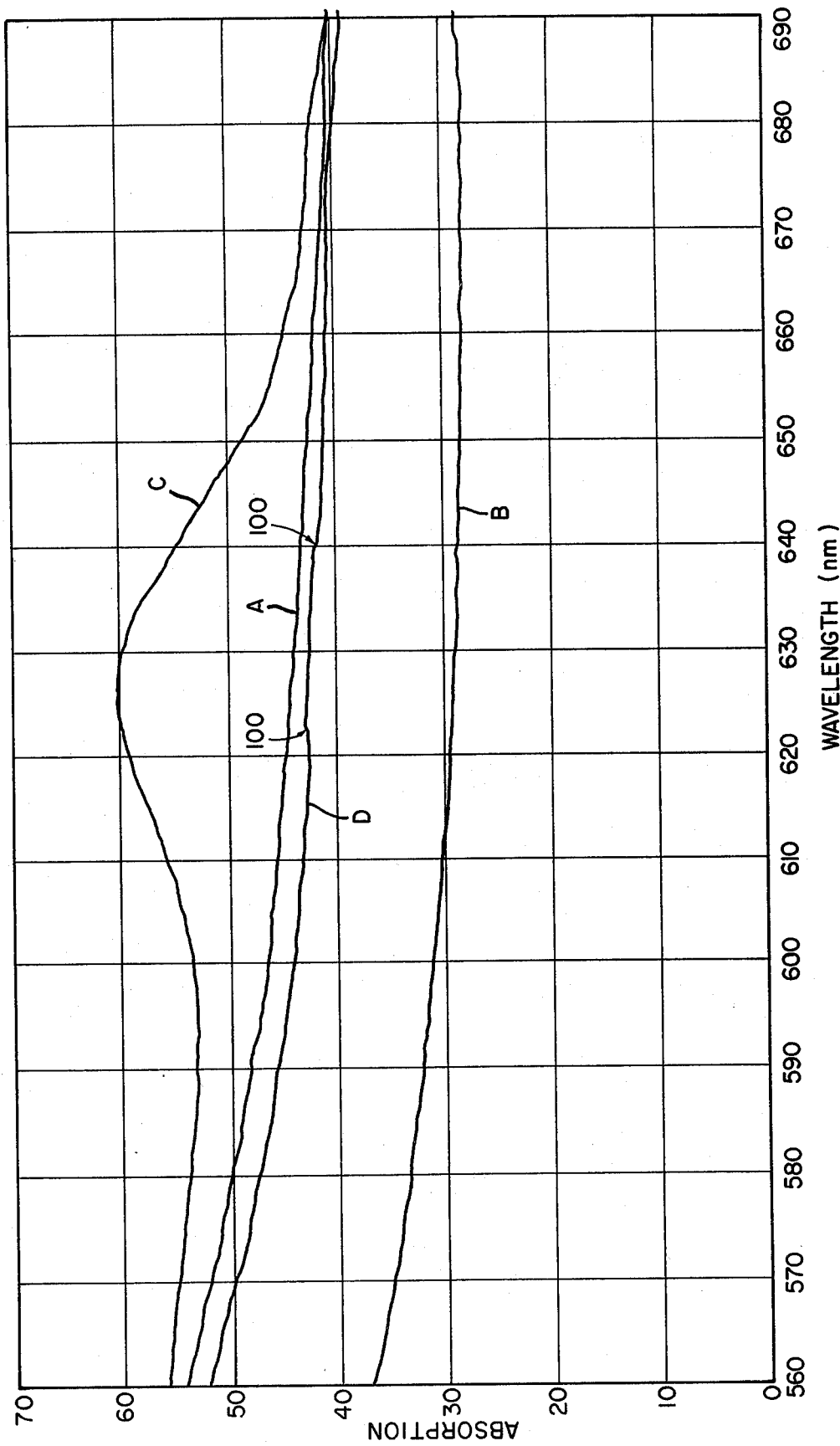
FIG. 3 depicts a series of spectral response curves relating to operation of the system of FIG. 1.

The operation of a photometer system in accordance with the invention may be more particularly realized from the following description made in reference to FIG. 3 in which there is illustrated a series of spectral response curves derived from different test ampoules. Curve A is the spectral response derived from a first normal (i.e. no dye present) ampoule plus contents. Curve B is also derived from a normal filled ampoule. It will be noted, however, that the traced curves of A and B, although substantially parallel are, however, displaced by a specific and substantially constant baseline magnitude factor, which could be due, for example, to variations in the normal (e.g. amber) glass ampoule color (i.e. the color of the glass container itself may vary from ampoule to ampoule). An additional reason which might cause a difference in "baseline" is the possible variation in position of the ampoules with respect to the light beam. Any system having as its purpose the aim of the present invention must, like the present invention, be able to cope with substantial baseline variation as demonstrated by curves A and B.

Curve C represents a leaky ampoule containing the minimum level of, for example, blue dye detectable by the human being under normal circumstances. Finally, Curve D is the spectral response of a leaky ampoule containing the lowest amount of blue dye concentration at which reliable detection can presently be made for relatively high-speed, high-volume throughput in accordance with the invention (i.e. at least a level of 1/10th the human eye detection capability). In curve D, at the points marked 100, there may be seen the relatively minute changes in magnitude from which a system in accordance with the invention may correctly reject that ampoule as leaky.

However, it is not sufficient to merely measure the absolute value of absorbance, particularly in view of the likelihood of baseline shift from ampoule to ampoule as is evidenced in FIG. 3 by Curves A and B. As shown, Curve A, though representative of a good ampoule, has a high baseline due perhaps to the container being of darker (amber) color. On the other hand although Curve D is derived from an ampoule containing a small amount of blue dye, this curve has a lower baseline than the good ampoule represented in Curve A. Were the system designed to merely measure absolute value of absorbance, it is conceivable that the ampoule represented by Curve D could be accepted whereas the good ampoule represented in Curve A would be rejected, with the threshold for rejection set, for example at an absorbance level (in FIG. 3) between Curves A and C for a particular wavelength such as 630 nm.

The system in accordance with the invention, rather, determines the absorbance value at the 630 nm point of the response curve and also determines the abosrbance value at another wavelength which is at times referred to herein as the reference wavelength ($\lambda$). The value of 630 nm should, of course, be chosen to optimize the detection of the blue dye. On the other hand, the reference $\lambda$ may be purposely chosen at a point on the spectrum far enough removed from the optimum blue dye $\lambda$ so as to eliminate possible cross effects. Further, it should generally be chosen at a point in the spectrum at which the response may be described as stable, i.e. no substantial magnitude variations in the spectral response curve due for example to the expected glass ampoule tint or the color of its contents.

The electrical signals derived respectively from the target (630 nm) region and the reference $\lambda$ (e.g. 690 nm) region are subtracted via the difference amplifier stage 11, e.g. the reference-wavelength value is subtracted from the target wavelength value.

Looking to FIG. 3, for Curve A which is representative of a good ampoule with high baseline, the difference value is nevertheless very small. For "bad" i.e. leaky ampoules, such as are represented in Curves C and D, the difference is greater, sufficiently so to trigger the threshold comparator 13. For Curve C it is apparent that the target and reference values are relatively grossly different, whereas in regard to Curve D the difference is just above the present minimum level of detection but nevertheless is above the empirically determined threshold established as the other input to comparator 13.

It will thus be apparent that this threshold determines the sensitivity of the invention. It is preferable that this threshold be adjustable. The threshold should not, for example, be so low in value as to reject good ampoules (i.e. senstitivity too high).

Apart from the technique described hereinbefore, the dye threshold could in practice instead be established as follows. The spectral response of several sample ampoules such as are represented in Curves A–D of FIG. 3 may be derived. In reviewing each of the curves in FIG. 3, as has been already noted, Curve D is determined to be close to the present minimum detection capability, and thus the associated difference value voltage (the output of stage 11) would be the basis for the threshold determination of comparator stage 13. One can typically set this threshold to have a voltage level input to stage 13 somewhere midway between the voltage levels output from stage 11 for the Curves A and D. It will be appreciated that in actuality the output of stage 11 for the ampoule represented in Curve A of FIG. 3 is practically zero.

It will also be appreciated that selection of the reference $\lambda$ and the target $\lambda$ will be different for each different application, i.e. for different sample material, different colored ampoule, different dye, etc., or any combination thereof. In accordance with the invention such changes are readily taken into consideration by merely changing the interference filters 5 and/or 6 (and, as appropriate, detectors).

For example, since on-the-fly detection is a key factor particularly in industrial environments, filters 5 and 6 can, as hereinbefore mentioned, be mounted on a rotary wheel employing N number of filter pairs which can be selected at will for any particular sample analysis. Such as arrangement could be used, for example, for providing multiple reference target pairs for each sample, to check for each of the constituents of the sample being present and that substances (e.g. the dye) which should not be there indeed are not. Moreover, one could by such an arrangement readily check to see that even the ampoule glass is of the correct color range and that the sample has not graded due, for example, to ultra violet light.

Other possible advantages to such a filter arrangement are that it lends itself to programming for fast (e.g. stepped) movement through all or selected ones of the N filter pairs. In this way, an operator could have a new sample processed very quickly to determine what wavelengths would be best for the reference wavelength(s). In such instance derivation of this information would likely come from the outputs of current-to-voltage converters 9 and 10.

System sensitivity may be optimized by a careful selection of the reference wavelength. It is best, for example, to select for a particular situation (i.e. in the case of a particular normal ampoule) a point on the response curve thereof at which no absorption peaks appear. In looking to FIG. 3, for example, such an area is particularly well defined at 690 nanometers for the curve A and B ampoules. In comparison, although there are no significant absorption peaks at say 550 nanometers, the increasing slope of the curves at this particular wavelength provides a less attractive reference wavelength than the 690 nanometer point, where the curves are all substantially horizontal, i.e. absorption is not significantly changing in magnitude with respect to $\lambda$, thus providing a more stable reference situation. The two major criteria that should be observed for reference $\lambda$ selection, then, are substantially flat baseline and minimal absorption.

The substantial difference in baseline represented in FIG. 3 between Curves A and B clearly shows varying color (e.g. amber) from ampoule to ampoule as encountered in an inspection line. It has been shown in the above that absent the technique of the present invention, the darker ones of these ampoules could be rejected even though they are, in fact, good (i.e. no dye present). The dual wavelength detector system according to the invention avoids this problem by providing compensation for variations in color from ampoule to ampoule.

It is to be understood that the rejection signals provided from either comparator 13 or AND gate 17 (FIG. 1) may be coupled to any suitable rejection mechanism, which may for example take the form of a pneumatic or mechanical system, for physically removing the rejected ampoules from the line.

It should be noted, too, that the difference circuit leg (diff. amp 11/comp. 13), with a suitably established dye threshold signal (i.e the difference between the input signals to stage 11 for a known good ampoule being zeroed-out), one can detect also empty ampoules as well as turbid/opaque ampoules.

A modified system will now be described, in connection with FIG. 4, in which the dye threshold level may be set or established other than manually.

Figure 4:
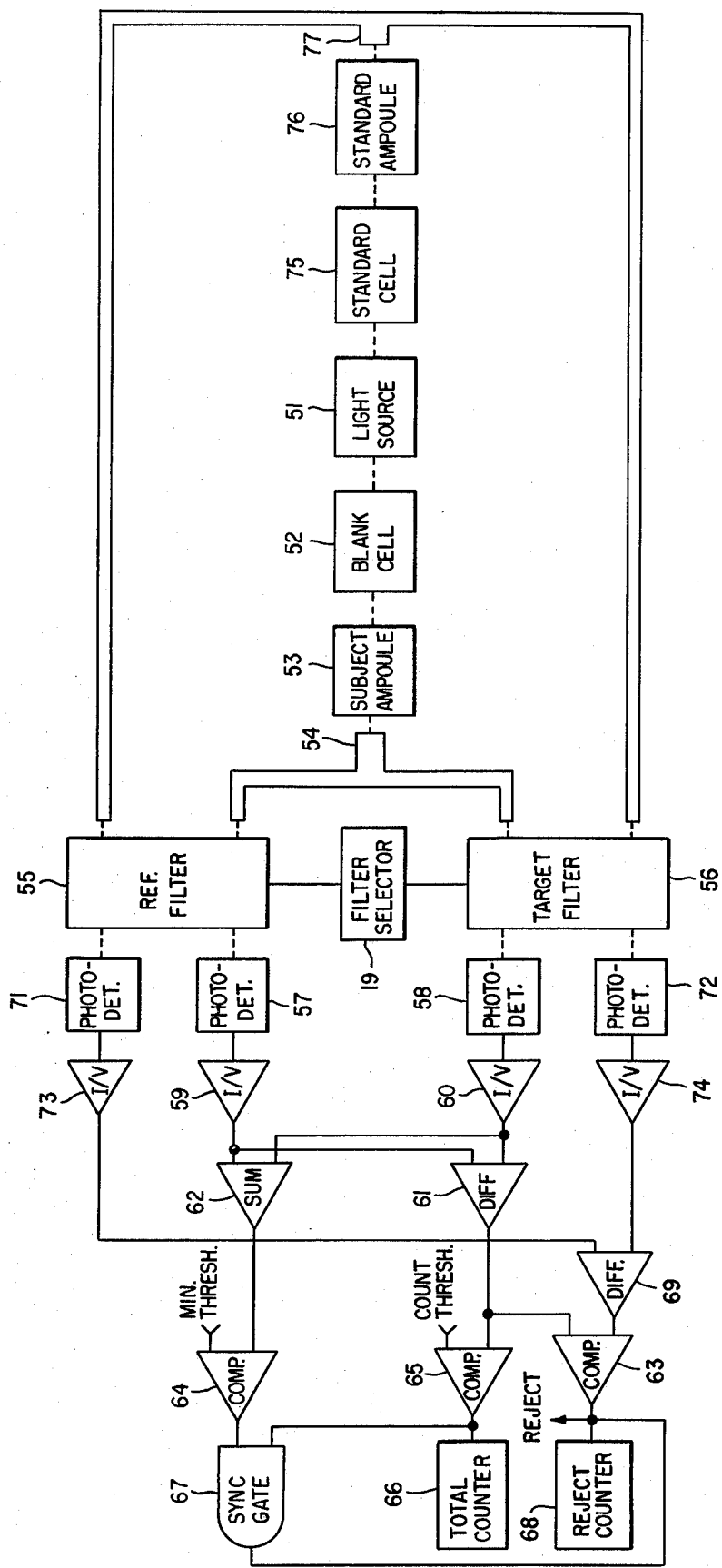
FIG. 4 is a schematic diagram of a modified arrangement of the system according to FIG. 1.

The inspection system of FIG. 4 utilizes a tungsten light source 51 to provide electromagnetic energy to be measured. Two cells 52 and 75 are placed in the light path. Cell 75 contains blue dye in the concentration (path length compensation used) that is the minimum one wishes to detect. Cell 52 has identical contents except for the blue dye, which compensates for any optical properties introduced by the cells. Ampoule 76 is a standardizing ampoule from the same production lot as those to be inspected but known to contain no dye (e.g. this ampoule was not processed through the dye bath leak test). Ampoule 53 is the subject ampoule being inspected.

Bifurcated fiber optics 54 and 77 evenly divide the optical signature of the ampoules 53 and 76 to the two filters 55 and 56. Photodetectors 57, 58, 71 and 72 convert the optical signatures to respective electric currents. It should be noted that detectors 57 and 58 are converting the optical signatures of ampoules being inspected and detectors 71 and 72 handle the standard ampoule.

Current to voltage converters 59, 60, 73 and 74 each change the current output of the respective photodetector to a voltage signal for use by the sum and difference amplifiers 62 and 61 respectively. Difference amplifier 61 yields the difference between the optical signals through the two filters 55 and 56 (which, as before, may be selected by a filter selecting arrangement 19) for the ampoule being inspected. This is an indication of the blue dye content within the ampoule 53. Summing amplifier 62 takes the sum of the optical signals through the two filters 55 and 56 for the ampoule being inspected. The sum signal is used as an indication of optical path blockage or system failure or of an empty or substantially underfilled ampoule.

Difference amplifer 69 is used to obtain the difference between the optical signature through the two filters 55 and 56 for the standard ampoule 76. This signal is used as the threshold which an inspected ampoule must remain below in order to be considered a "good" ampoule. Whether or not the inspected ampoule signature (from difference amplifier 61) exceeds the standard (from differential amplfier 69) is determined by a comparator 63. The comparator controls the reject means (not particularly shown) and the reject counter 68.

Comparator 65 compares the inspected ampoule difference signal (from differential amplifier 61) to a set threshold in order to establish a signal indicating the presence of an ampoule being inspected and to increment the total counter 66. Comparator 64 compares the inspected ampoule summation signal from summing amplifier 62 to a set threshold in order to establish the existence of for example an optical path failure or an empty/grossly underfilled ampoule. This signal is transmitted to the synchronizing gate 67, as is the count signal from comparator 65 and on to the reject means and reject counter 68.

The reject means may, again, be any suitable means of flagging or physical removal of the "reject" ampoules. It may for instance involve the use of a delay system (asynchronous or synchronous to the transport) if the inspection point and rejection point are physically removed from each other.

Such a system as described above provides an immunity to certain problems that can arise in the course of an inspection run. These may include but are not necessarily limited to:
1. lamp intensity shifts
2. lamp spectral shifts
3. sample spectral changes due to degradation
4. differences between lots of ampoules within a given product line (lot=1 production run).

System capability may be broadened also by substituting for the difference amplifier stage 11 of FIG. 1 a log ratio stage that effectively takes the difference of the logarithms of the two input signals to that stage. Alternatively, stages 9 and 10 could, instead of being linear I/V converters, comprise logarithmic converters. In such instance, stage 11 would remain as originally described.

A principal effect of the above-mentioned alternatives is that the logarithms are taken of the electrical signals originally output from stages 9 and 10 and the ratio of these logarithms effected, to provide an output signal which is proportional to the concentration of material examined (which, or course, could contain blue dye). This ratio is then fed to stage 13 for comparison with the established threshold (for the dye) of comparator 13.

With this added capability the ampoules under inspection could be categorized, on the basis of the intensity of the output signal from stage 11, as to the degree of leakage (in the case of blue dye) and/or the amount of material concentration, and/or even the amount of material degradation, as example.

It should be noted also that situations can arise where the contents of the ampoule are quite close in terms of spectral response to that of the glass ampoule itself, and this can make the distinction of minor changes in the contents very difficult. The characteristics (e.g. non-linearly) of a logarithmic function, on the other hand, make it particularly suitable as a separation means in signal processing in such close situations. This point is amplified hereinafter.

Figure 5:
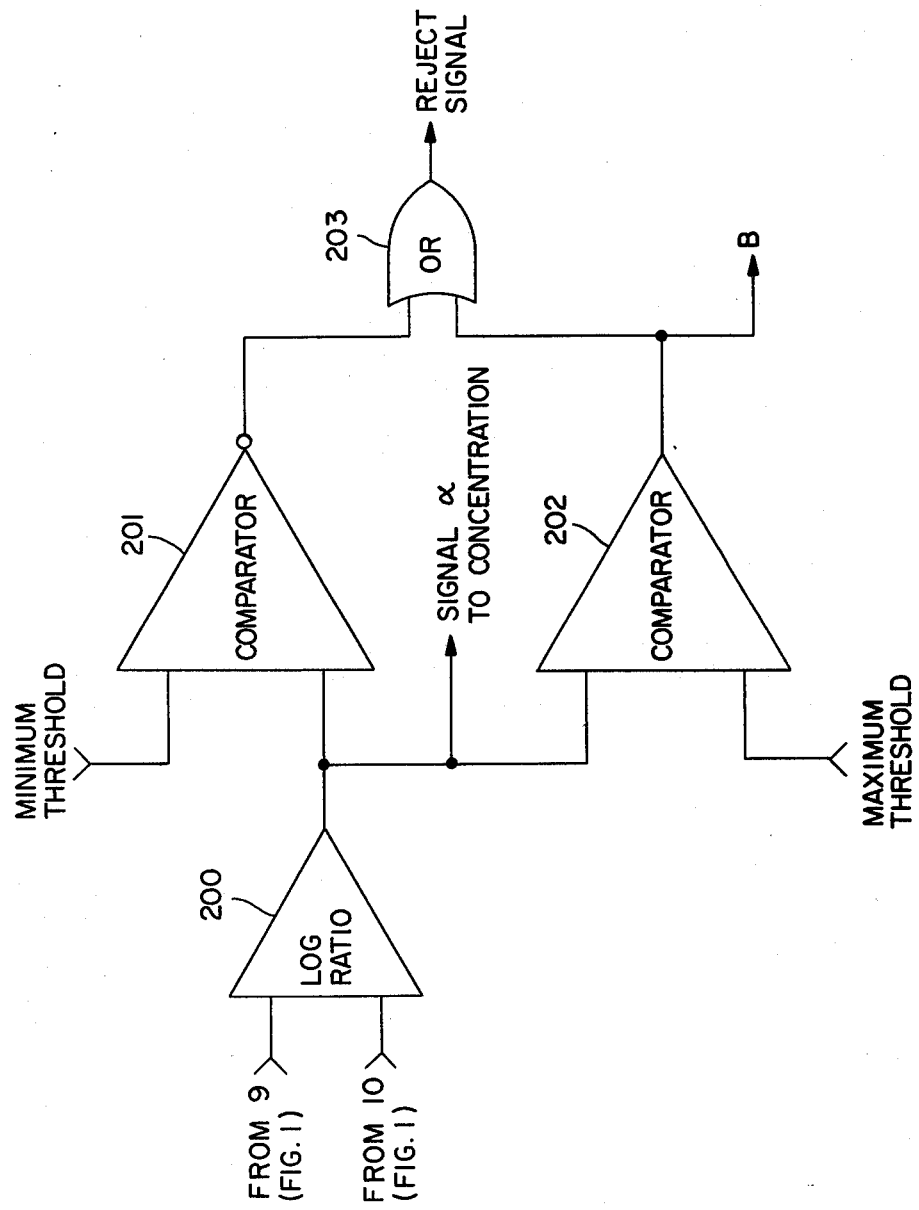
FIG. 5 is a schematic diagram of another modification of the system according to FIG. 1.

In connection with the application of the invention in determining (the sufficiency of) the concentration of the subject material in the ampoule per se, the arrangement of FIG. 1 may be modified in accordance with that of FIG. 5 to provide a pair of thresholds, in lieu of an expensive elaborate and complex arrangement otherwise required to pinpoint the exact level of concentration. The first of these thresholds establishes a point above which it may be considered that the contents are of too high a concentration and the other accordingly that the ampoule contents have too low a concentration. Thus, any ampoule falling between the two thresholds would be considered acceptable. There can now automatically be determined whether the concentration of the ampoule contents per se is acceptable simply by determining whether the concentration-proportional signal falls between the two well-defined limits.

Referring to FIG. 5, the outputs from I/V converters 9 and 10 (of FIG. 1) are connected to a log ratio unit 200, the output of which is, as aforesaid, proportional to concentration. This output is in turn coupled to a pair of comparator units 201 and 202. The other input to comparator 201 would be the minimum threshold. The output of comparator 201 may be fed via an OR gate 203 to a rejection counter (such as counter 18 in FIG. 1) and/or to a rejection mechanism.

With regard to comparator 202, the other input thereto it would be the maximum threshold established (e.g. empirically) in regard to the units under inspection. As with the output of comparator 201, stage 202 is connected via OR gate 203. The arrangement of comparators 201, 202 together with OR gate 203 may be thought of as comprising a "window" comparator. The output of the window comparator of FIG. 5, is in the form of a rejection signal yet is representative of the concentration of the contents of the ampoule under inspection, i.e. the concentration of that ampoule is determined to be outside of the min/max window limits if an output from OR gate 203 is generated.

Since the output of log ratio unit 200 is proportional to the concentration of the contents under inspection, this signal itself may be tapped off (as shown in FIG. 5), for example for a more precise determination of the concentration of the ampoule contents.

A particular case of substantial interest which may be dealt with by way of the arrangement of FIG. 5 is the aforementioned situation where the spectral response of the ampoule contents and the glass ampoule itself are substantially similar, i.e. both absorb in substantially the same wavelength region(s) of their respective absorbance versus wavelength curves. One can add to this consideration the prospect that the only significant portion of the "signature" of the particular ampoule contents appears on a or the substantially non-linear portion of the absorbance/wavelength curve (i.e. in an area where absorption magnitude is varying substantially with λ). The situation can be further complicated by considering that there occurs substantial variation in color between ampoules made of the same material.

Figure 6:
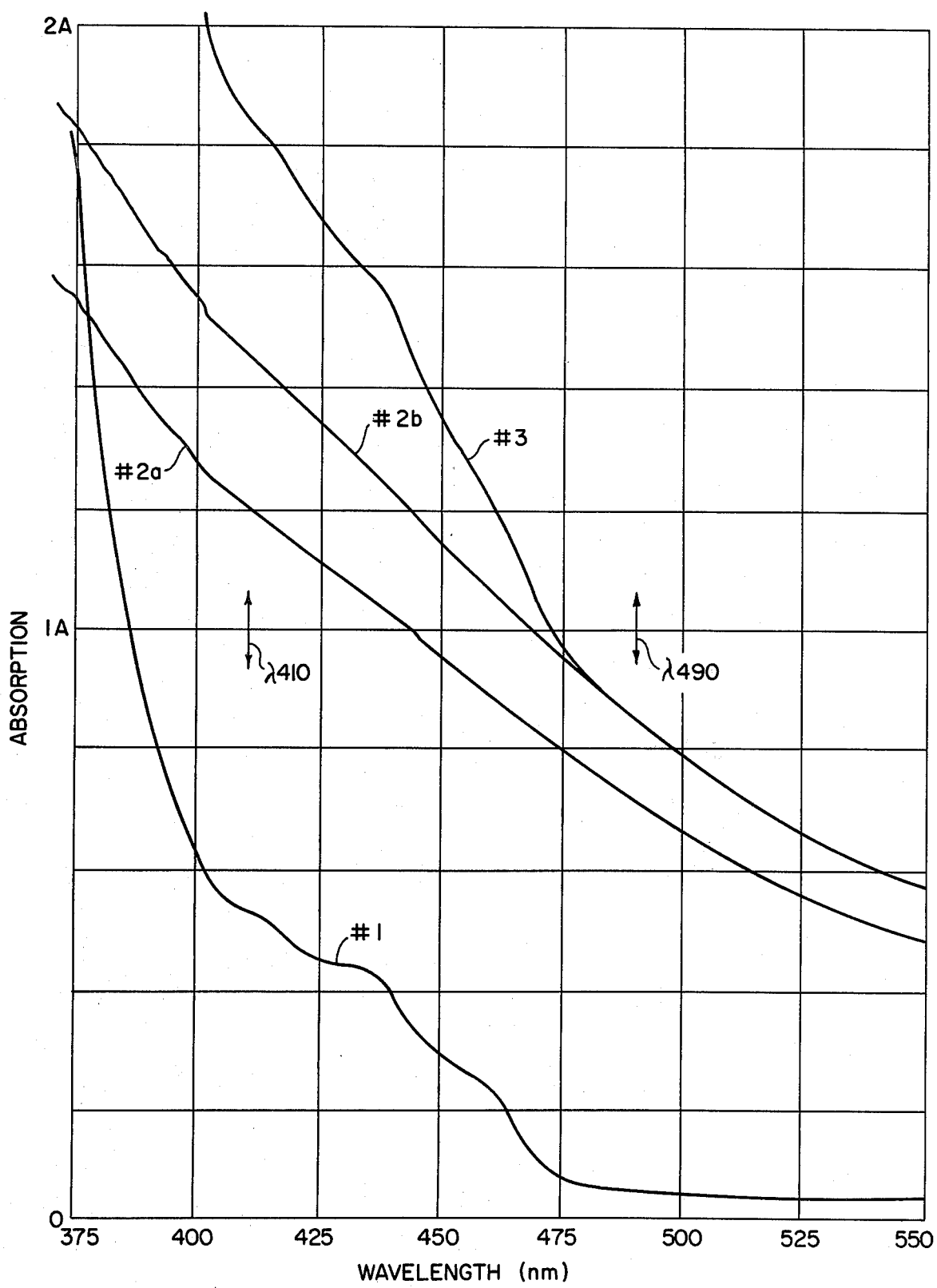
FIG. 6 graphically illustrates a substance having the significant portion of its signature located on a relatively high sloping portion of the response curve and "masked" significantly by the response curve of the ampoule itself.

Specifically, the aim, then, is to measure nondistructively the concentration values inside sealed ampoules (e.g amber ampoules) of a substance bearing spectral properties as, for example, shown in the graphic illustration of FIG. 6. In FIG. 6 both the curves for the substance (curve #1) and amber glass (curves #2a and 2b), as well as the curve for the combination thereof (curve #3), are shown. It may be seen that the amber glass absorbance is roughly one at 490 nm and greater than one at 410 nm. This means that the amber glass is absorbing more than the 90% of the measurement light. The variation in amber glass is large, as is indicated by displacement between the various water-blank amber ampoules represented by curves 2a and 2b. It can also be seen in FIG. 6 (Curve #1) that the substance absorbs usefully in the 450 to 410 nm range; however, quantization is extremely difficult (about 100 times more difficult) than detection of say blue dye at a point in the spectrum where the amber glass slightly absorbs light (i.e., 630 nm and 690 nm). Under such conditions, it is all too likely that a simple subtraction of the transmission signals, as discussed hereinbefore e.g. in connection with blue dye detection, would not be powerful enough to adequately separate say ±10% concentration situations from the specified strength. However, if the logarithims of the two signals are taken and then subtracted, the output, as aforesaid, is proportional to the concentration. Note Beer's law which states $$A = \log \frac{1}{T} = abc = \log \frac{I\lambda_1}{I\lambda_2} = \log I\lambda_1 - \log I\lambda_2$$

Where
A = absorbance
T = transmittance
a = molar absorption coefficient
b = absorption path length in cm
c = concentration in moles/liter
$I\lambda_1$ = intensity at $\lambda_1$
$I\lambda_2$ = intensity at $\lambda_2$.

Nevertheless, the concentration determination for the substance depicted in FIG. 6 is deemed difficult enough (due to a highly sloping amber ampule curve in the useful absorbance range of the substance) that it is desirable to employ for example a microprocessor or other inexpensive calculating means to take the logarithm of the two signals and then calculate a correction based for example on an empirically determined correction curve.

For less difficult determinations, however, taking the logs of the two signals and then taking the difference is entirely adequate to readout a signal directly proportional to concentration (e.g. blue dye concentration could be read directly to quantitate the amount of leakage).

It is to be understood, in connection with the above discussion, that for certain applications, it may be of advantage to use in place of a log ratio module a factorial module or some other analog multifunctional operator stage, short of a digital processor, particularly in instances where one wishes to correct for a substantial sloping baseline.

What is claimed is:

1. A dual wavelength spectrophotometer for use in connection with container content inspection and in particular container leak detection, comprising in combination:

(a) a source of radiant energy;
(b) first means arranged to receive radiant energy from said soure which has passed through the container and its contents for generating simultaneously identical signals constituting optical signatures of the container and its contents;
(c) a plurality of predeterminably selected unique radiant energy filter means arranged to each receive a said optical signal from said first means;
(d) a plurality of photodetector means arranged with said filter means for providing a plurality of respective output electrical signals representative of the radiant energy received from said filter means;
(e) second means for determining the difference between at least a selected first pair of said respective output electrical signals and comparing said difference with a pre-established first threshold value; and
(f) third means for determining the sum of at least a selected first pair of said respective output electrical signals and comparing said sum with a pre-established second threshold value.

2. The combination of claim 1 wherein said third means includes means for generating an output signal leading to the rejection of the container under inspection in the event said sum fails to reach said second threshold value.

3. The combination of claim 2 wherein said second threshold value is selected to effect a rejection signal in the event of occurrence of any one of: a foreign object being inspected, a container having substantially opaque contents being inspected, a substantially underfilled container being inspected, and system failure occurring at any operative point prior to the comparison of said sum and said pre-established second threshold value.

4. A double wavelength spectrophotometer for use in connection with container content inspection and in particular container leak detection, comprising in combination:

(a) a source of radiant energy;
(b) first means arranged to receive radiant energy from said source which has passed through the container and its contents for generating simultaneously a plurality of substantially identical optical signals constituting optical signatures of the container and its contents;
(c) a plurality of predeterminably selected unique radiant energy filter means arranged to each receive a said optical signal from said first means;
(d) a plurality of photodetector means arranged with said filter means, for providing a plurality of respective output electrical signals representative of the radiant energy received from said filter means; and
(e) second means for determining the sum between at least a selected first pair of said respective output electrical signals and comparing said sum with a pre-established first threshold value, wherein an output signal is effected from said second means in the event said sum fails to exceed said threshold.

5. A dual wavelength spectrophotometer for use in connection with container content inspection and in particular container leak detection, comprising in combination:

(a) a source of radiant energy;
(b) first means arranged to receive radiant energy from said source which has passed through the container and its contents for generating simultaneously a plurality of substantially identical optical signals constituting optical signatures of the container and its contents;

(c) a plurality of predeterminably selected unique radiant energy filter means arranged to each receive a said optical signal from said first means;

(d) a plurality of photodetector means arranged with said filter means for providing a plurality of respective output electrical signals representative of the radiant energy received from said filter means; and (e) a pair of second means for determining the difference between at least a selected first pair of said respective output electrical signals and comparing said difference with a pre-established first threshold value, one of said second means being arranged to detect the presence of a preselected impurity substance within the container's contents and the other of said second means being arranged to determine the correctness of color of the container's contents even in the absence of said impurity substance.

* * * * *